(12) United States Patent
Dalton, Jr. et al.

(10) Patent No.: US 6,654,652 B1
(45) Date of Patent: Nov. 25, 2003

(54) CALIBRATION AND SECURITY DEVICE FOR PC AUDITORY PROGRAMS

(75) Inventors: Leslie W. Dalton, Jr., Valdosta, GA (US); Robert Brian French, Valdosta, GA (US)

(73) Assignee: Beiersdorf AG, Hamburg (DE)

( * ) Notice: Subject to any disclaimer, the term of this patent is extended or adjusted under 35 U.S.C. 154(b) by 601 days.

(21) Appl. No.: 09/644,516

(22) Filed: Aug. 23, 2000

(51) Int. Cl.[7] .................. G06F 17/100; H04R 29/00; A61B 5/00

(52) U.S. Cl. .................. 700/94; 381/60; 381/107; 600/559; 73/585

(58) Field of Search .................. 381/60, 57, 58–59, 381/104–107; 600/558, 559; 700/94; 73/585

(56) References Cited

U.S. PATENT DOCUMENTS

| | | | | |
|---|---|---|---|---|
| 5,999,856 A | * | 12/1999 | Kennedy | 607/57 |
| 6,167,138 A | * | 12/2000 | Shennib | 381/60 |
| 6,322,521 B1 | * | 11/2001 | Hou | 600/559 |
| 6,366,863 B1 | * | 4/2002 | Bye et al. | 702/57 |
| 6,396,930 B1 | * | 5/2002 | Vaudrey et al. | 381/60 |
| 6,447,461 B1 | * | 9/2002 | Eldon | 600/559 |
| 6,549,630 B1 | * | 4/2003 | Bobisuthi | 381/94.7 |

* cited by examiner

*Primary Examiner*—Forester W. Isen
*Assistant Examiner*—Laura A. Grier
(74) *Attorney, Agent, or Firm*—Norris McLaughlin & Marcus, P.A.

(57) ABSTRACT

This invention comprises a hardware and software system for automatically calibrating the audio output level of a personal computer used to evaluate human hearing. The invention requires hardware in the loop, which has the added benefit of preventing unauthorized use of the software.

6 Claims, 2 Drawing Sheets

CALIBRATION AND SECURITY DEVICE FOR PC AUDITORY PROGRAMS

BACKGROUND

1. Field of Invention

This invention relates to the field of hearing testing and analysis. More specifically, the invention comprises a hardware and software system for automatically calibrating the audio output level of a personal computer used to evaluate human hearing. The requirement of hardware in the loop has the added benefit of rendering unauthorized copies of the software unusable.

2. Description of Prior Art

Audio testing equipment has long been used to diagnose human hearing problems. Recent advances, particularly with the advent of computer controls, have allowed the diagnosis of many conditions beyond simple hearing loss. Hypersensitivity to sound is a major symptom in the diagnosis of disorders such as central auditory processing dysfunction (CAPD), attention deficit hyperactivity dysfunction (ADHD), attention deficit disorder (ADD), pervasive development dysfunction (PDD), dyslexia, autism, and others. The testing equipment must be accurately calibrated so that the sound pressure produced for the test corresponds to known levels used in other testing.

Hearing testing has traditionally been performed by audio technologists. However, modern personal computers have made it possible for testing to be conducted by non-professionals. Many personal computers now have sophisticated audio input and output capabilities ("sound cards"). With the proper software, these computers are capable of conducting relatively sophisticated tests. However, running the same software on different computers will result in a variety of sound output levels. This disparity results from the fact that the different computers have different sound cards, different speakers, etc. In order for diagnostic software to be run on a variety of computers, it is therefore necessary to provide a universal calibrating technique.

The known devices for administering sophisticated hearing tests are therefore limited in that they:

1. Require the use of specifically designed and calibrated testing equipment;
2. Can only be run by an audio technologist; or
3. In the case of software-based systems, do not provide for calibration of the personal computer audio output in order to comply with known sound levels.

Objects and Advantages

Accordingly, several objects and advantages of the present invention are:

1. To provide a system which can be run on commonly available personal computers;
2. To provide a system which can be run by a person having no specialized training as an audio technician;
3. To provide a system which can automatically calibrate the sound output level for virtually any personal computer;
4. To provide a system which is relatively inexpensive; and
5. To provide a system which requires hardware in the loop, thereby rendering unauthorized copies of the software unusable.

DRAWING FIGURERS

REFERENCE NUMERALS IN DRAWINGS

| | | | |
|---|---|---|---|
| 2 | personal computer | 4 | hardware module |
| 6 | speaker port | 8 | microphone port |
| 10 | speaker input | 12 | microphone output |
| 14 | connector cable | 16 | headphone/microphone jack |
| 18 | headphone | 20 | microphone |
| 22 | comparator | 24 | reference voltage |
| 26 | first isolation switch | 28 | second isolation switch |
| 30 | third isolation switch | 32 | fourth isolation switch |
| 34 | test subject | | |

Description

The proposed invention is intended to allow a personal computer to perform all the functions of the standard audiometric hardware used in the diagnosis and treatment of hearing-related disorders. Standard audiometric hardware is carefully calibrated to provide specified sound pressure levels to the test subject. Although a conventional personal computer has sophisticated audio input and output devices, it has no calibration mechanism capable of regulating its audio output to meet the specified sound pressure levels. The proposed invention adds this capability to many different types of computers.

Figure 1:
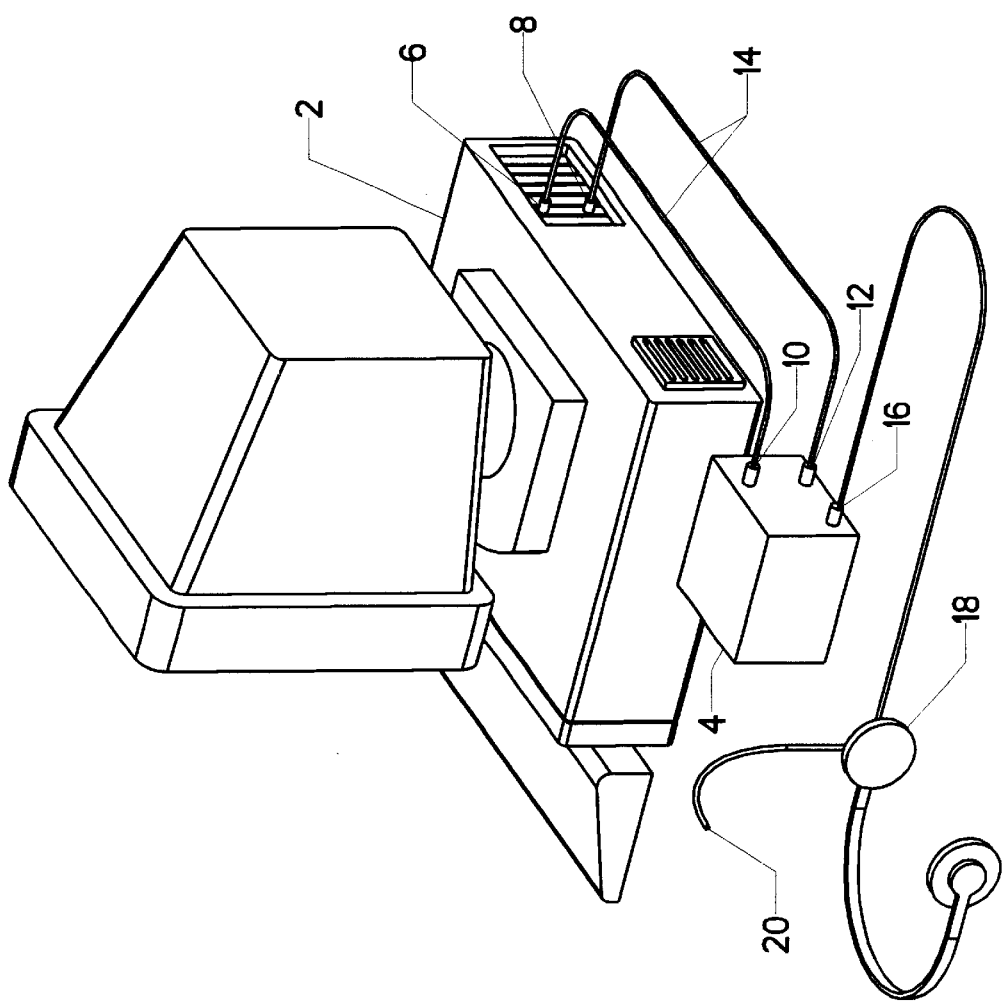
FIG. 1 is an isometric view, showing the hardware component of the device and its connection to a personal computer.

FIG. 1 illustrates the invention's major components. Personal computer 2 has numerous input and output connections, generally located on its rear surface. Among these connections are speaker port 6 and microphone port 8. Speaker port 6 provides an audio output. It is typically connected to a set of headphones, or to a power amplifier connected to a speaker. Microphone port 8 is typically connected to a microphone or other audio input device.

Hardware module 4 is placed near personal computer 2. Hardware module 4 is depicted as having a significant size for ease of illustration. After reviewing this description, it will be readily apparent to those skilled in the art that hardware module 4 could be made much smaller than the example illustrated. Hardware module 4 has speaker input 10, which is connected via a connector cable 14 to speaker port 6. Hardware module 4 also has microphone output 12, which is connected via a connector cable 14 to microphone port 8.

Headphones 18 and microphone 20 are shown as an integral unit, though they can be separate. They are connected to hardware module 4 at headphone/microphone jack 16. Headphone/microphone jack 16 actually incorporates two signal carriers in a single connection, as will be apparent in the schematic.

The audiometric test subject wears headphones 18 and microphone 20. Testing software running on personal computer 2 administers a variety of diagnostic tests to the subject. The tests may be interactive, with the subject both hearing and making verbal responses.

Figure 2:
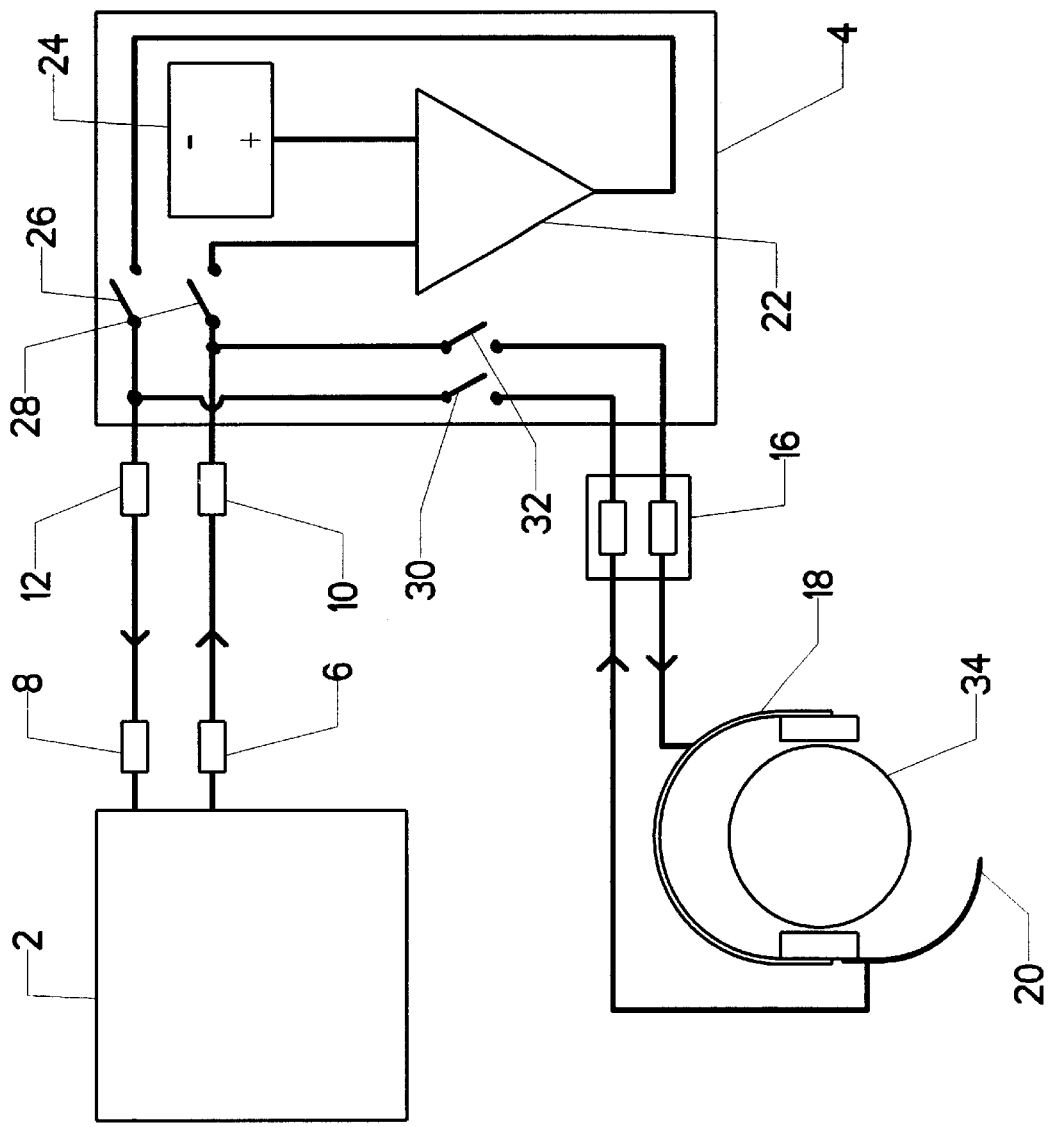
FIG. 2 is a schematic view, showing the operation of the calibration device.

FIG. 2 is a simplified schematic detailing the operation of the proposed invention. Hardware module 4 contains comparator 22. Comparator 22 has two input lines and a single output line. The first input line is connected to speaker port 6 on personal computer 2. Second isolation switch 28 selectively makes and breaks this connection. The second input line is connected to reference voltage 24. Reference voltage 24 is a fixed DC source. It can be produced by a rectifying power supply. However, as it is only needed for short periods, a small battery has been found to be adequate for long operation.

The output line of comparator 22 is normally in the off state; i.e., it has no voltage until the voltage on the first input line rises to the level of the voltage on the second input line (reference voltage 24). When the voltage on the two input lines becomes equal, comparator 22 applies voltage to the output line, thereby sending a trigger signal to microphone port 8.

The operation of the invention will now be described in its normal sequence. When the unit is first powered "ON", first isolation switch 26 and second isolation switch 28 are in the closed position. Third isolation switch 32 and fourth isolation switch 34 are in the open position. Thus, comparator 22 is connected to personal computer 2, whereas headphones 18 and microphone 20 are not.

At this point, software running on personal computer 2 initiates a sinusoidal calibration signal on speaker port 6. This calibration signal is of a unique nature that will not be inadvertently produced by running other programs. The software initiates the calibration signal with the computer's output volume set at a very low level. Then, the software slowly increases the computer's output volume so that the amplitude of the calibration signal increases. As this occurs, the voltage on the first input line of comparator 22 is increasing. At some point, the voltage on the first input line of comparator 22 will equal reference voltage 24, at which point comparator 22 will turn on its output line and send a trigger signal to speaker port 6.

The software running on personal computer 2 is continually scanning for the receipt of the trigger signal on speaker port 6. When this signal is received, the software will immediately cease increasing the computer's output volume and lock it in the position where the input lines to comparator 22 are balanced. The software then ceases the transmission of the calibration signal. At this point, control means are employed to open first isolation switch 26 and second isolation switch 28, thereby isolating comparator 22 from personal computer 2. At or about the same time, control means are employed to close third isolation switch 32 and fourth isolation switch 34. Thus, headphones 18 are connected to speaker port 6, and microphone 20 is connected to microphone port 8.

At this point, the audio output signal of personal computer 2 has been calibrated to provide the correct sound pressure levels to test subject 34. Those skilled in the art will realize that a specific type of headphone 18 and microphone 20 must be employed to make the calibration truly accurate. The effect of the comparator circuit is to take a software-generated calibration signal (which will be the same on every computer), and adjust the computer's output volume so that the same output voltage is obtained at headphones 18 regardless of the variations in amplification equipment from computer to computer. This calibrated output voltage is then used to power a standard set of headphones so that each user receives the same standardized sound level.

Previously in this disclosure, control means for opening and closing the various isolation switches were mentioned. These control means can be of different types. In the simplest embodiment, hardware module 4 is configured so that when it is first powered on, first isolation switch 26 and second isolation switch 28 are in the closed position. Likewise, third isolation switch 32 and fourth isolation switch 34 are defaulted to the open position. At the point where comparator 22 sends the trigger signal on its output line, a simple timing circuit is initiated. This circuit will immediately open first isolation switch 26 and second isolation switch 28. A short duration later, the same timing circuit will close third isolation switch 32 and fourth isolation switch 34. The delay is employed to prevent the calibration signal from being transmitted through headphones 18 to test subject 34. As timing circuits are well understood by those skilled in the art, this circuit has not been illustrated schematically.

As those skilled in the art will also appreciate, a simple timer type of control means is rather crude. However, as the computer being used should remain calibrated for an extended period, it is not necessary to run the calibration cycle very often. Even so, a more sophisticated control means may be desirable. Since the audiometric testing is being conducted by software running on personal computer 2, it makes sense to use this software as the control means for regulating hardware module 4. A digital interface may be provided between the two, which would allow the software running on personal computer 2 to control the four isolation switches located in hardware module 4. With this embodiment, the software could be used to periodically recalibrate the computer's output volume.

The interaction of personal computer 2 and hardware module 4 also acts as a theft-deterrent for the audiometric software. The audiometric software is typically stored on a CD. This CD contains the executable code as well as certain sound samples which are critical to the testing. As inexpensive CD copying equipment is now available, the possibility of unauthorized copying of the software exists. In such an event, it will be impossible to use the duplicate CD without having hardware module 4. This feature results from the fact that the audiometric software, prior to running any of its functions, initiates the calibration signal on speaker port 6. It will not run its functions until it has received the trigger signal back from hardware module 4 on microphone port 8. Thus, an individual who has possession of the audiometric software but not hardware module 4 will be unable to run the audiometric software.

Summary, Ramifications, and Scope

Accordingly, the reader will appreciate that the proposed invention allows the calibration of a personal computer's output volume so that the personal computer generates a specified sound pressure level in a set of headphones. The invention has further advantages in that 1. provides a system which can be run by a person having no specialized training as an audio technician;
2. provides a system which can automatically calibrate the sound output level for virtually any personal computer;
3. provides a system which is relatively inexpensive; and
4. provides a system which requires hardware in the loop, thereby rendering unauthorized copies of the software unusable.

Although the preceding description contains significant detail, it should not be construed as limiting the scope of the invention but rather as providing illustrations of the preferred embodiment of the invention. For example, many types of control switches or circuits could be used in hardware module 4 without altering the central objective of the invention. Thus, the scope of the invention should be fixed by the following claims, rather than by the examples given.

Having described my invention, I claim:

1. A device for calibrating the sound output level on a computer having a microphone port and a speaker port, comprising:

a. a reference voltage producing device;

b. a comparator, having a first input, a second input, and an output, wherein said first input is connected to said speaker port of said computer, said second input is connected to said reference voltage producing device, and said output is connected to said microphone port of said computer, and wherein a trigger signal is generated on said output when said first input becomes equal to said second input;

c. means for generating an increasing audio signal on said speaker port of said computer; and d. means for fixing said sound output level on said computer at a constant level upon said computer receiving said trigger signal on said microphone port from said comparator.

2. The device as recited in claim 1 wherein said means for generating an increasing audio signal on said speaker port of said computer comprises a software program running on said computer.

3. The device as recited in claim 1 wherein said means for fixing said sound output level on said computer at a constant level upon said computer receiving said trigger signal on said microphone port from said comparator comprises a software program running on said computer.

4. The device as recited in claim 3, wherein said software program further comprises a plurality of hearing diagnostic tests, and wherein said software program will not perform said hearing diagnostic tests until said software program receives said trigger signal.

5. The device as recited in claim 3 wherein said switch control means comprises a software program running on said computer.

6. The device as recited in claim 1, further comprising:

a. a first switch placed between said first input of said comparator and said speaker port of said computer;

b. a second switch placed between said output of said comparator and said microphone port of said computer;

c. a set of headphones;

d. a microphone;

e. a third switch, switchably connecting said speaker port to said set of headphones;

f. a fourth switch, switchably connecting said microphone port to said microphone; and g. switch control means for closing said first and second switches and opening said third and fourth switches during the time period when said increasing audio signal is being produced, and for opening said first and second switches and closing said third and fourth switches after said trigger signal has been generated by said comparator, so that said comparator is disconnected from said speaker port and said microphone port, said set of headphones is connected to said speaker port, and said microphone is connected to said microphone port.

\* \* \* \* \*